US008678638B2

(12) United States Patent
Wong

(10) Patent No.: US 8,678,638 B2
(45) Date of Patent: Mar. 25, 2014

(54) PROCESS BAG CONTAINER WITH SENSORS

(75) Inventor: Dennis Wong, Dedham, MA (US)

(73) Assignee: EMD Millipore Corporation, Billerica, MA (US)

( * ) Notice: Subject to any disclaimer, the term of this patent is extended or adjusted under 35 U.S.C. 154(b) by 28 days.

(21) Appl. No.: 13/043,862

(22) Filed: Mar. 9, 2011

(65) Prior Publication Data
US 2011/0249526 A1    Oct. 13, 2011

Related U.S. Application Data

(60) Provisional application No. 61/339,751, filed on Mar. 9, 2010.

(51) Int. Cl.
B01F 15/00       (2006.01)
(52) U.S. Cl.
USPC .......................................................... 366/142
(58) Field of Classification Search
USPC ............................................. 366/150.1, 142
See application file for complete search history.

(56) References Cited

U.S. PATENT DOCUMENTS

| 4,681,378 | A | * | 7/1987 | Hellman, III | 312/223.2 |
| 7,384,783 | B2 | | 6/2008 | Kunas et al. | |
| 7,603,921 | B2 | | 10/2009 | Baumfalk et al. | |
| 2005/0163667 | A1 | | 7/2005 | Krause | |
| 2005/0272146 | A1 | | 12/2005 | Hodge et al. | |
| 2006/0118472 | A1 | | 6/2006 | Schick et al. | |
| 2006/0131765 | A1 | | 6/2006 | Terentiev et al. | |
| 2006/0240546 | A1 | | 10/2006 | Goodwin et al. | |
| 2007/0126794 | A1 | | 6/2007 | Schick et al. | |
| 2007/0159920 | A1 | * | 7/2007 | Baumfalk et al. | 366/152.4 |
| 2007/0292940 | A1 | * | 12/2007 | Roll | 435/288.7 |
| 2009/0135667 | A1 | * | 5/2009 | Terentiev et al. | 366/142 |
| 2009/0147617 | A1 | | 6/2009 | Baumfalk et al. | |
| 2010/0261260 | A1 | * | 10/2010 | Morgan | 435/257.3 |

FOREIGN PATENT DOCUMENTS

| DE | 102006001623 A1 | 7/2007 |
| DE | 102006018824 A1 | 10/2007 |
| WO | 2008/016411 A1 | 2/2008 |
| WO | 2008/101124 A1 | 8/2008 |
| WO | 2009/059645 A1 | 5/2009 |
| WO | 2009/120269 A2 | 10/2009 |

OTHER PUBLICATIONS

International Search Report received for PCT Application No. PCT/US2011/027692 mailed on Aug. 18, 2011, 5 pages.

(Continued)

Primary Examiner — Tony G Soohoo
Assistant Examiner — Anshu Bhatia
(74) Attorney, Agent, or Firm — EMD Millipore Corporation

(57) ABSTRACT

A process bag container is provided comprising a flexible bag, at least one inlet sealed to the bag, and an outlet. A probe housing for a probe construction is sealed to the bag. Preferably, the probe housing extends at least partway into the bag interior and is connected to a cable for power and data transmission that runs along the outer surface of the bag to the top of the bag or its support container. The probe construction is adapted to monitor the composition of a reagent in the bag as well as the environment within the bag. A mixer is positioned within the bag to effect mixing of reagents in the bag.

9 Claims, 6 Drawing Sheets

(56) References Cited

OTHER PUBLICATIONS

International Written Opinion received for PCT Patent Application No. PCT/US2011/027692, mailed on Aug. 18, 2011, 6 pages.

International Preliminary Report on Patentability received for PCT Patent Application No. PCT/US2011/027692, mailed on Sep. 20, 2012, 5 pages.

* cited by examiner

US 8,678,638 B2

PROCESS BAG CONTAINER WITH SENSORS

CROSS-REFERENCE RELATED APPLICATIONS

This application claims the benefit of U.S. Provisional Patent Application No. 61/339,751, filed on Mar. 9, 2010 the entire contents of which are incorporated by reference herein.

BACKGROUND OF THE INVENTION

This invention relates to a process bag container utilized to mix reagent ingredients, to sense the characteristics of the resultant mixture and to dispense the resultant mixture.

Presently, a wide variety of reagents including cell culture supplements, buffers, media or the like are utilized in the biotechnology industry in producing and purifying biological products such as protein. The reagents are generally produced from two compositions at least one of which is a liquid. The biological products produced with these reagents are required to be produced under conditions to avoid product contamination.

Presently, process bag containers are formed from a flexible polymeric material and are adapted with inlets which permit introduction of reagents into the container and an outlet to dispense a mixture of the reagents from the container. The bag generally is provided with a mixing device such as an impeller that is connectable to a power source such as a magnetically coupled motor so that it can be rotated thereby to promote mixing of the reagents within the container. Other devices may use top mounted stirrers or impellers on a shaft that extends into the bag through a journal. In use, the flexible container is placed within a rigid housing that supports the container so that reagent mixing followed by dispensing can be effected.

Since reagents utilized in the production of biological products must be accurately controlled or monitored regarding their composition such as pH, conductivity, oxygen content, or temperature, it is desirable to provide a means for measuring such composition and environmental values during reagent mixture production.

Accordingly, it would be desirable to provide a process bag container which permits mixing of reagents therein. In addition, it would be desirable to provide such a container which permits monitoring the composition of a reagent within the container in which the reagent is produced. Furthermore, it would be desirable to provide such a container which does not have its wall compromised during production and monitoring of the reagent within the container. Additionally, it would be of benefit to provide a probe that does not require the rigid housing to be modified such as with holes to access protruding sensors and route cable connections.

Lastly, most sensors are long and extend inward horizontally to a tank. This often requires a large amount of space on the interior and exterior of the tank to accommodate the sensor(s). Additionally, there is need for alignment of the bag with the rigid container so that the sensor ports are in register with each other and accessible to the user. These protruding elements are also subject to bumping, misalignment, calibration loss and damage. A new design is desired that minimizes the risk to the sensor(s) and providing a more compact assembly so as to minimize the length to which a sensor protrudes past the bag outline.

SUMMARY OF THE INVENTION

In accordance with this invention, a process bag container is provided for mixing reagents therein and subsequently dispensing the reagent mixture therefrom. The process bag container includes a bag sized to store a desired amount of reagent, at least a first inlet for supplying the container with one or more reagents and optionally a second or more inlet for supplying one or more other reagents to the container. The container includes one or more probe housings which protrude into the bag space and which contain a probe sealed to the outer surface of the container bag and a mixer that is sealed to or extends through the container wall in a liquid tight manner. The mixer mixes the reagents in the container. The probe measures characteristics of composition and/or environment in the container. The mixer is connected to a power supply so that it can affect its desired function. The probe is connected to an external meter for power and display and processing of measurement information. The container also is provided with an outlet so that the mixed reagent can be delivered to a desired point of use. In one embodiment, the outlet is sealed during reagent mixing so that a dead zone of reagent is not formed in the outlet during reagent mixing.

DESCRIPTION OF SPECIFIC EMBODIMENTS

The process bag container of this invention is useful for mixing two or more reagents and subsequently dispensing the reagent mixture to a desired point of use. Representative suitable reagents comprise a mixture of buffers or the like. Likewise, this could be used as bioreactor if desired.

Figure 1:
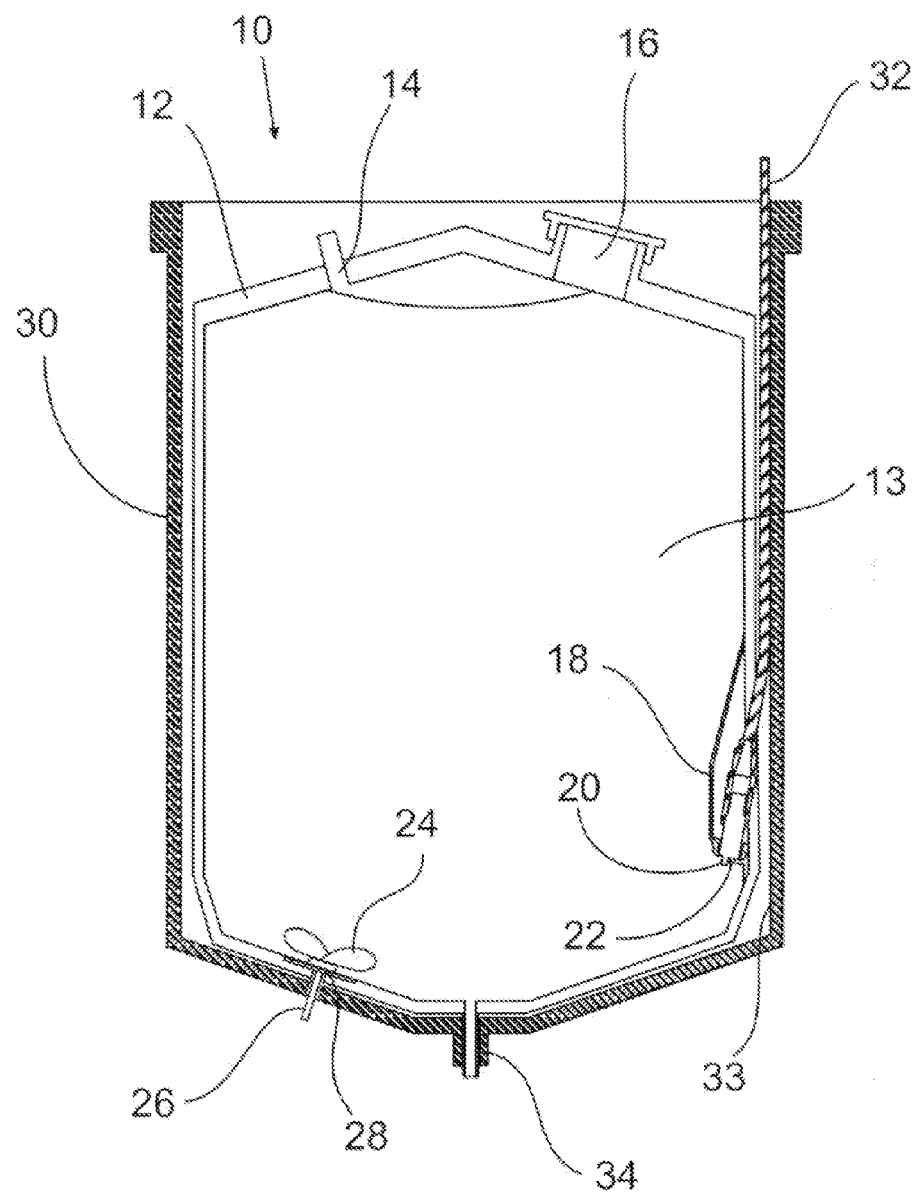
FIG. 1 is a cross section view of the process bag container including a probe housing of this invention positioned within a relatively rigid housing.
Figure 2:
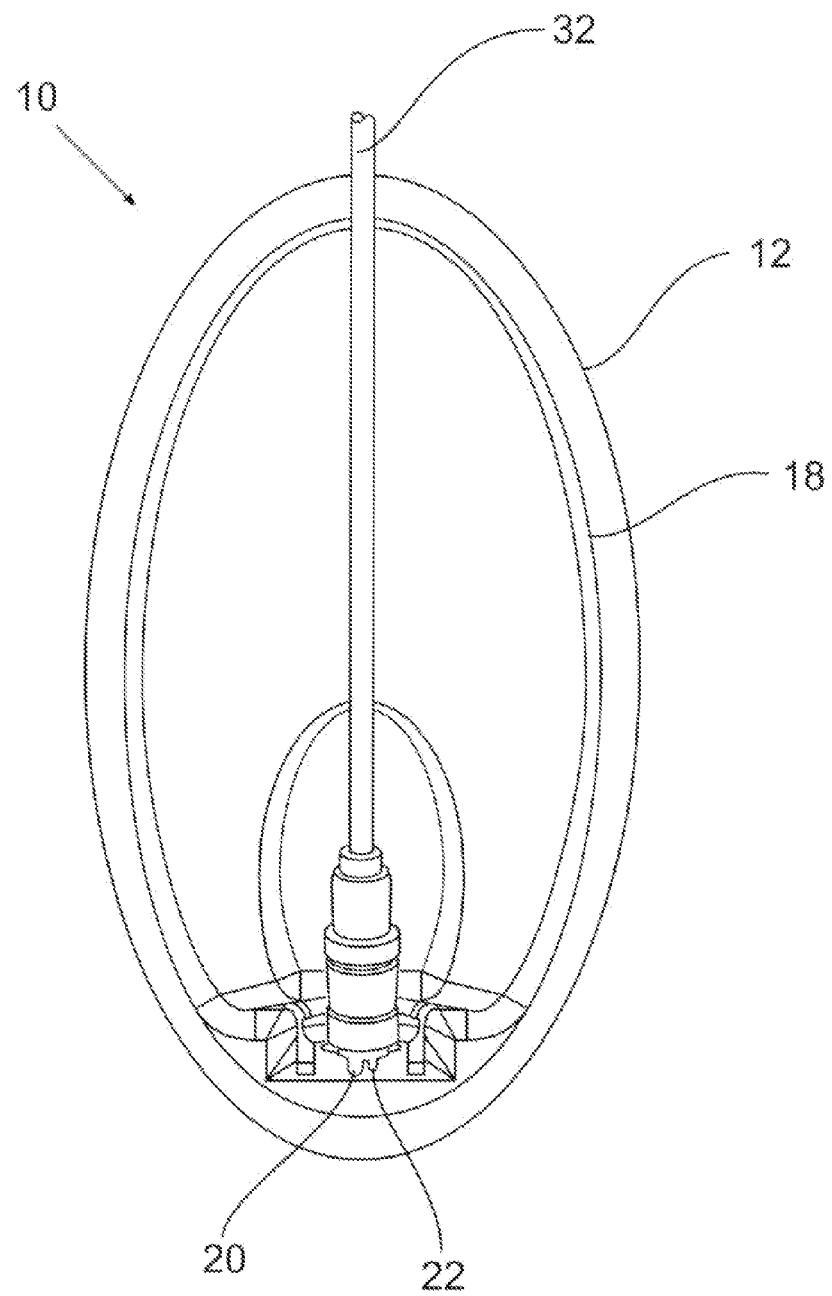
FIG. 2 is a front view of the probe housing shown in FIG. 1.

Referring to FIGS. 1 and 2, the process bag container 10 includes a bag 12, a first inlet 14 sealed to the bag 12 and a second inlet 16 sealed to the bag 12. This setup is for a bag in which at least one liquid and a powder are to be mixed. Liquid would enter through the first inlet 14 and powder through the second inlet 16. Alternatively, when two or more liquids are being mixed with no powder, either a single port such as 14 or 16 may be used or two identical ports, preferably like that of inlet 14 can be used. In these drawing the inlet(s) and outlet may or may not be shown as being sealed off from the exterior. However that is the intent of the present invention to provide a presterilized closed bag system that is then connected upstream and downstream to other components via a sterile connector such as the Lynx® STS connector of Millipore Corporation.

The bag 12 is formed of a flexible polymeric composition such as silicone, polyethylene, polypropylene, blends or laminates of such plastics or the like. One such multilayered film bag is the PureFlex™ bag from Millipore Corporation which is made of polyethylene.

The container 10 is provided with a probe housing 18 which is sealed to the outside or inside surface of the bag 12 in a manner which prevents leakage of reagents from the bag 12. The probe housing 18 is provided with one or more probes 20 and 22 which are precalibrated to effect the desired measurement of a composition and/or environment within the bag 12. Desirably, the probes 20, 22 are gamma stable so they can be gamma sterilized with the bag 12 to which it/they are attached. The probes 20 and 22, probe housing 18 and bag 12 are for a single use so that they can be discarded after the desired use.

Figure 3:
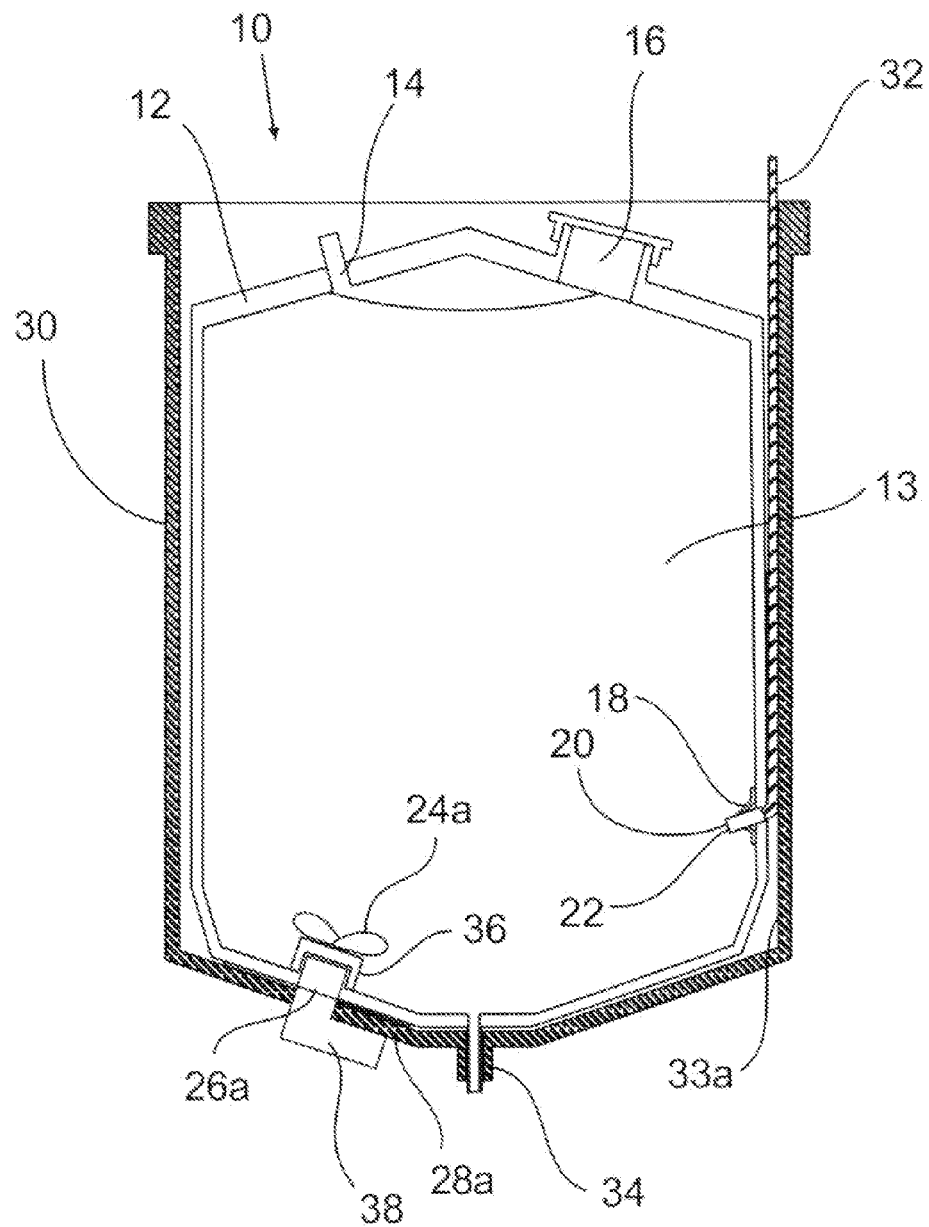
FIG. 3 shows an alternative embodiment in partial cross sectional view.

The bag 12 also is provided with a mixer such a impeller 24 mounted on a rotatable axle 26 (FIG. 1) which, in turn, is positioned in the bag 12 via a port 28 that extends through support housing 30 in a manner that prevents leakage from the bag 12. Alternatively one may use an impeller 24a mounted to a magnetic couple 36 that is attached via magnetism to a magnetic drive mechanism 38 as shown in FIG. 3. The port 28a is configured to the magnetically driven impeller assembly (24a and 36) and may either be magnetically levitated above the port's 28 surface or attached by a post to the port 28 (not shown) or supported by a bearing on the inner surface of the coupler 36 (not shown) or be retained in a cup that extends into at least a portion of the port 28 such as is known in the art.

Support housing 30 is formed of a rigid composition such as polypropylene, stainless steel, polyethylene, fiberglass, or the like to provide support for the bag 12.

Figure 5:
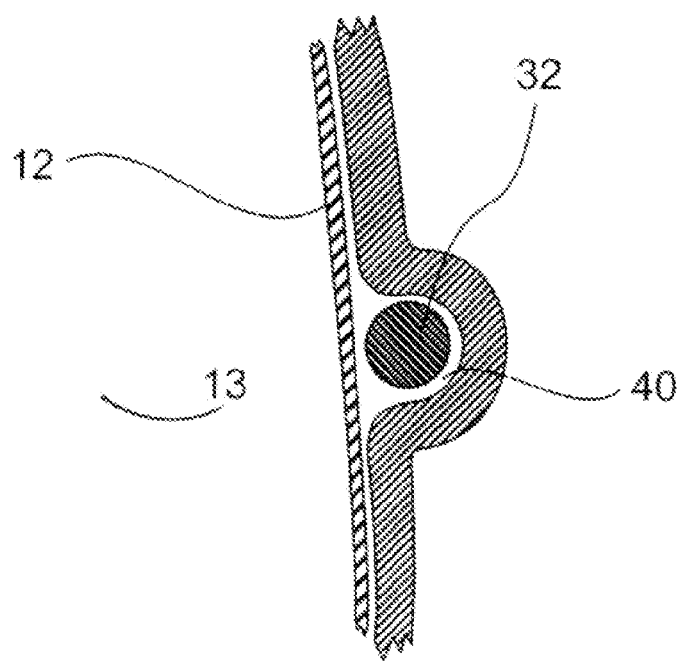
FIG. 5 shows a portion of the bag and support housing relating to the cable channel.

The probes 20 and 22 are connected to cable 32 which provides power to the probes 20 and 22 and directs measurements from the probes 20 and 22 to a measuring apparatus (not shown). The cable 32 runs along the inside of the support housing 30 between the exterior of the bag 12 and the interior wall 33 of the support housing 30. Optionally, the interior wall 33 of the support housing can have a channel 40 formed in it in which the cable 32 may lay so as to eliminate any inward bulge along the vertical wall of the bag 12 where the cable 32 is run as shown in FIG. 5. Thus, the characteristics of the reagent and the environment within the bag 12 can be monitored over time.

The probe housing 18 may be a separate plastic piece formed of a plastic that is compatible with and can bond to the bag material. Generally, it may be a thermoplastic material such as polyethylene or polypropylene or any other plastic that is compatible with and can bond to the bag. Preferably it is heat sealed to the bag material. Alternatively, it may be glued or solvent bonded or welded (such as by ultrasonic welding) to the bag 12.

As shown in FIGS. 2 and 6A-C, the probe housing can be in the form of an oval although other shapes, such as circular, square, rectangular, hexagonal and the like can also be used.

The housing 18 has an outer edge or lip 19 that is used to seal the housing 18 in a liquid tight manner to the inner edge of an opening in the container 10 by the methods discussed above.

Figure 6A:
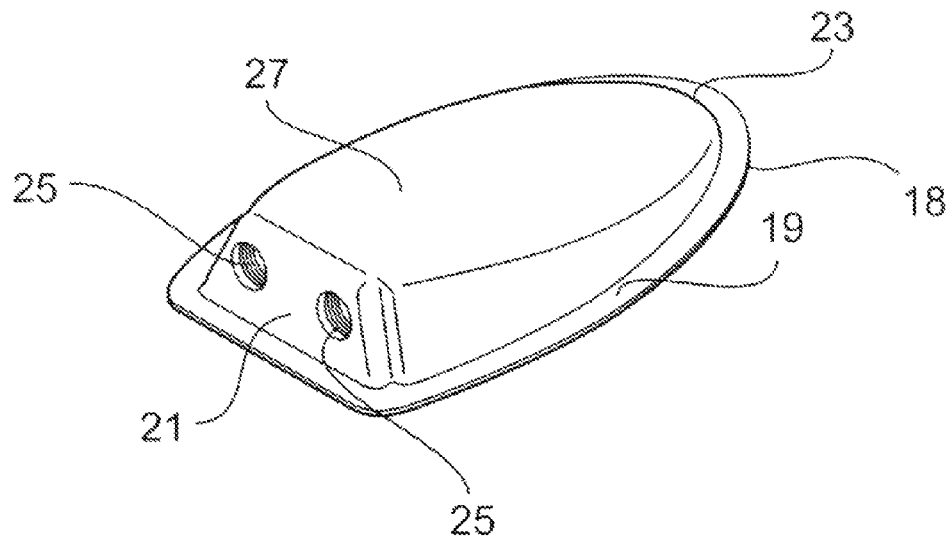
FIGS. 6A, B, and C show the probe housing.
Figures 6B, 6C:
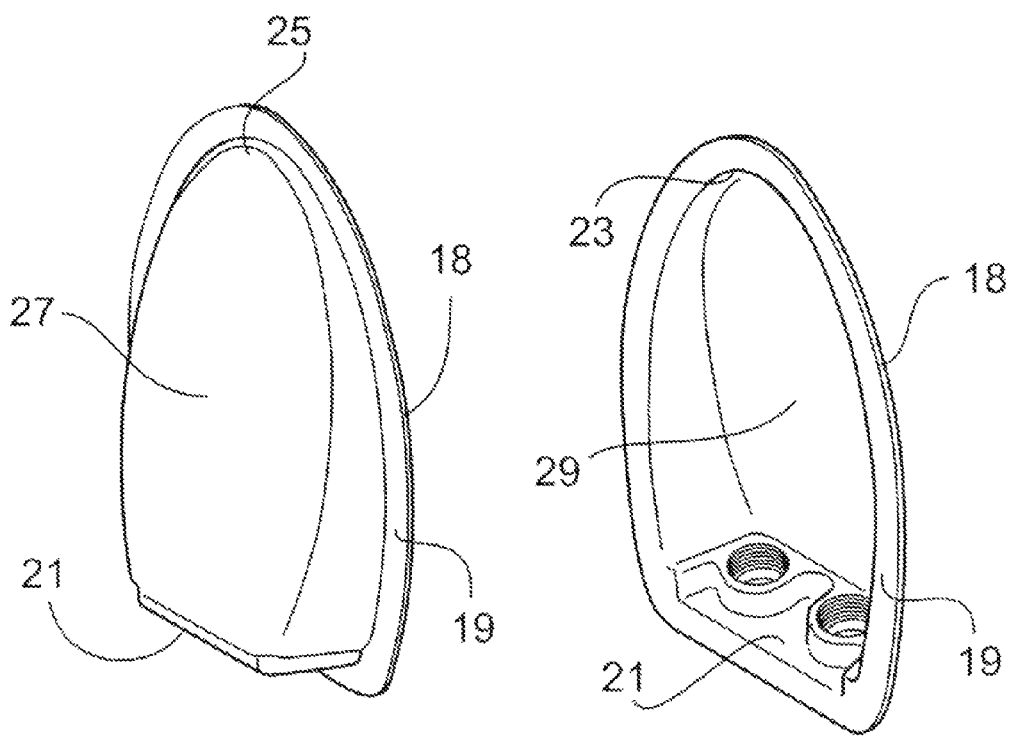

In one embodiment, such as in FIGS. 6A-C, the housing tapers such that the inner surface of the housing 18 at its lowermost point 21 extends further into the container 10 than the top point of the housing 23. In another embodiment it tapers the opposite way (not shown) so that the upper point extends out further into the bag than the lowermost point of the housing 18. In another embodiment there is no taper (not shown) and the housing extends inwardly equally from top to bottom and preferably from side to side as well.

For those sensors that are gravity dependent or affected by gravity in their readings the use of the embodiment where the sensor is located in the lower portion 21 of the housing 18 is preferred. In other embodiments the sensor may enter from the top 23 of the housing 18. In further embodiments it may enter along any portion of the housing surface.

FIG. 2 shows a one sensor port housing 18 while those of FIGS. 6A-C show a housing 18 having two sensor ports 25.

FIG. 6A shows the housing 18 with the inner surface 27 of the housing 18 uppermost. FIG. 6B shows the same housing as FIG. 6A but oriented as it might be attached to a container 10 with the lowermost point 21 extending further into the container 10 than the top point 23. FIG. 6C shows the outer surface 29 of the housing and again shows one preferred taper design for the housing 18.

Figure 4A:
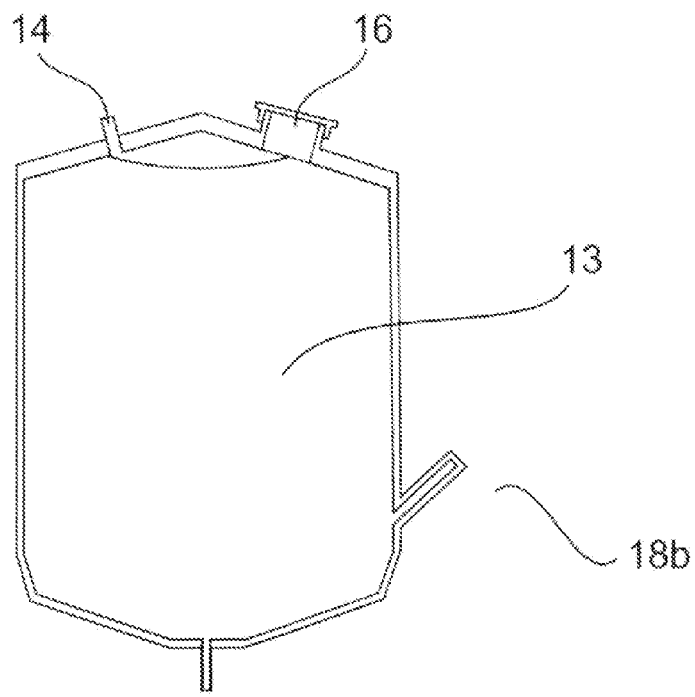
FIGS. 4A and B show an alternative version of the bag of the present invention in cross-sectional view.
Figure 4B:
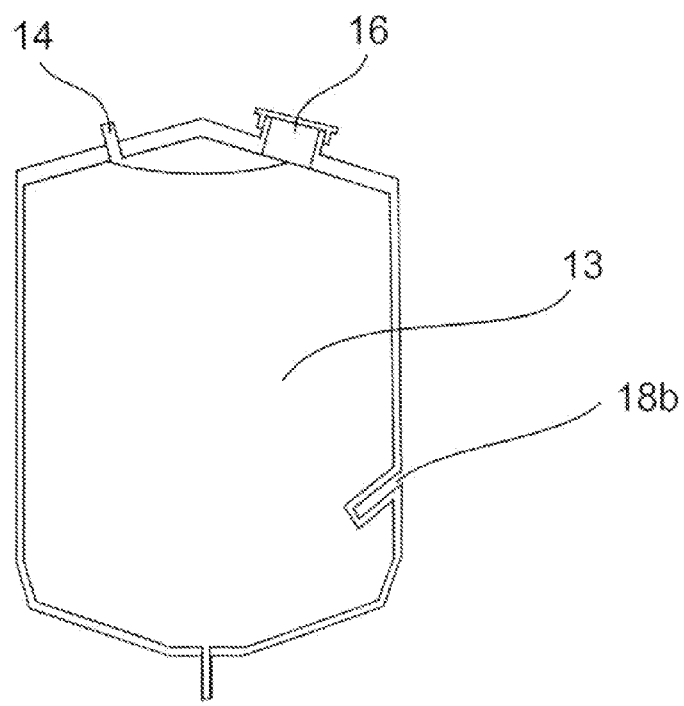

In another embodiment of FIGS. 4 A and B the probe housing 18b may be formed as part of the bag 12 itself. In FIG. 4A is shown the bag as it is being formed with the probe housing 18 being cut with the bag 12 and extending outwardly from the bag interior 13. In FIG. 4B, the probe housing 18 has been inverted on itself so that it now extends into the bag interior 13.

The probe may be attached to the port in different ways depending on the sensor design.

Preferably, the probe may be attached to the port by a threaded feature. Such thread feature in the port will have a liquid tight seal such as a threaded pathway in which the sensor has the corresponding mating thread. A gasket or O-ring may also be used between the sensor threads and the sensor port opening 25 to provide additional liquid tight sealing.

An alternative design may be the use of a separate threaded retaining nut that attaches to the sensor. This retaining nut would compress an o-ring or gasket against the sensor opening in the port to create a liquid seal.

In another design the probe may be sealed or potted in place.

The sensor would be attached to the port before gamma irradiation and remain in place afterwards to keep a sterile and liquid seal.

As shown in FIGS. 1 and 2, the probe housing 18 has a slightly inward protrusion into the interior space 13 of the bag 12. This allows for the probe(s) 20, 22 to accommodated at least in part within the interior of the bag 12 reducing the amount of room required for the probes 20, 22 in the support housing 30 or exterior to the support housing 30. Additionally, as shown the probes 20, 22 and probe housing 18 have a downward slope to them so that the extent to which the probes extend into the bag is controlled such that the probe housing 18 and/or probes 20, 22 do not adversely affect the mixing characteristics of the fluid(s) and/or solids in the bag 12.

Alternatively as shown in FIG. 3, the probe housing 18a may extend substantially horizontally into the bag interior 13. Likewise if desired, the probe housing 18 may have an upward slant (not shown) essentially being the reverse of the downward shape shown in FIG. 1.

The present invention minimizes the number of openings required in a support housing. This allows one to modify the bag with the probes in the desired positions while using a common support housing. This reduces the need for a specialized support housing. Additionally, when a heating or cooling jacket is used, it reduces the loss of insulation caused by the additional ports or openings that had been previously required.

Likewise this invention minimizes the extent to which the probes may extend outwardly beyond the support housing, minimizing the risk of damage to them in use.

Additionally, by allowing the probes to extend into the bag 12 by a small distance, one gets more accurate and representative data samples by avoiding the stagnant boundary layer that can form at the bag interior face.

Example 1

A Mobius® mix bag (200 liters volume) available from Millipore Corporation had two openings cut in its side opposite each other approximately 12 inches above the bottom of the bag. The opening in this example was oval and was made to match the housing shape except for the outer lip area. In this instance, the oval was 8 inches high and 5 inches wide with a flat bottom portion as shown in FIG. 2. The openings were made by simply tracing the design of the housing to the bag and cutting them out with a knife. The outer lip of each housing was heat sealed to the plastic of the bag to form a liquid tight seal. The sensor head for pH in one housing and conductivity in the other housing were attached and sealed by a threaded connection and an O-ring in the sensor port (Mettler Toledo sensors were used).

The bag was then tested with air for integrity and then placed into a Mobius Mix support container available from Millipore Corporation.

200 liters of reverse osmosis water was added to the bag and the pH, temperature and conductivity was read. A predissolved solution 1 L of 1M NaCl was added to the bag. The mixer was started at 550 rpm and pH, temperature, and conductivity were monitored over time until all reached a stable plateau number at about 30 seconds. This indicated that the solution had thoroughly mixed into the water. The mixer was shut off and the values were taken again in about 2 seconds. Verification of the measurement accuracy was done by inserting benchtop style pH and conductivity probes into a port at the top of the bag. The results indicated that the sensor port design and sensors were accurate and reliable enough to indicate the reacted state of the solution without the need to breach the bag to insert probes.

50 milliliters of 1 molar NaOH was added to the bag and the mixer ran at 550 rpm until the sensors provided a stable reading (about 30 seconds). The mixer was shut off and the readings taken again which were instantaneous agreed with those taken during the mixing. Verification of the measurement accuracy was done by inserting benchtop style pH and conductivity probes into a port at the top of the bag. The results indicated that the sensor port design and sensors were accurate and reliable enough to indicate the reacted state of the solution without the need to breach the bag to insert probes.

50 milliliters of 1 molar Hcl was added to the bag and the mixer ran at 550 rpm until the sensors provided a stable reading (about 90 seconds). The mixer was shut off and the readings taken again which were instantaneous and which agreed with the ones taken during mixing.

Verification of the measurement accuracy was done by inserting benchtop style pH and conductivity probes into a port at the top of the bag. The results indicated that the sensor port design and sensors were accurate and reliable enough to indicate the reacted state of the solution without the need to breach the bag to insert probes.

The invention claimed is:

1. A process bag container comprising:
a flexible bag,
an inlet conduit sealed to the bag,
an outlet conduit sealed to the bag,
a probe housing sealed to an exterior or interior surface of said bag, the probe housing having one or more probe ports and the probe housing extends fully into the interior of the bag,
a one or more probe apparatus for taking a measurement of a reagent in said bag, each of the one or more probe apparatus being positioned within a probe port of said probe housing such that the one or more probe apparatus are fully contained within the interior of the bag,
a cable for supplying power to said each of the one or more probe apparatus,
a mixing apparatus for mixing said reagent positioned within said bag
a means for supplying power to said mixing apparatus and
a support housing outside the bag for supporting the bag during use and a raceway formed in the inner surface of the support housing for the power cable.

2. The process bag container of claim 1 wherein said one or more probe apparatus comprises a plurality of probes.

3. The process bag of claim 1 wherein the probe housing extends into the bag interior at a downward angle.

4. The process bag of claim 1 wherein the probe housing extends into the bag interior at an upward angle.

5. The process bag of claim 1 wherein the probe housing extends into the bag interior at a substantially horizontal angle.

6. A process bag container comprising:
a flexible bag,
one or more inlets sealed to the bag,
an outlet sealed to the bag,
a probe housing sealed to an exterior or interior surface of said bag, the probe housing having one or more probe ports and the probe housing extends fully into the bag interior,
one or more probe apparatus for taking a measurement of a reagent in said bag, each of the one or more probe apparatus being positioned within a probe port of said probe housing,
a cable for supplying power to said each of the one or more probe apparatus,
a mixing apparatus for mixing said reagent positioned within said bag,
a means for supplying power to said mixing apparatus and
a support housing outside the bag for supporting the bag during use and a raceway formed in the inner surface of the support housing for the power cable.

7. The process bag of claim 1 wherein the probe housing extends into the bag interior at a downward angle by a taper to the housing such that the inner surface of the probe housing at its lowermost point extends further into the bag interior than the top point of the probe housing.

8. The process bag of claim 1 wherein the probe housing extends into the bag interior at an upward angle by a taper to the housing such that the inner surface of the probe housing at its upper point extends further into the bag interior than the lowermost point of the probe housing.

9. A process bag container comprising:
a flexible bag,
one or more inlets sealed to the bag,
an outlet sealed to the bag,
a probe housing sealed to an exterior or interior surface of said bag, the probe housing having one or more probe ports and the probe housing extends fully into the bag interior at a downward angle,
one or more probe apparatus for taking a measurement of a reagent in said bag, each of the one or more probe apparatus being positioned within a probe port of said probe housing such that the one or more probes are fully contained within the interior of the bag,
a cable for supplying power to said each of the one or more probe apparatus,
a mixing apparatus for mixing said reagent positioned within said bag,
a means for supplying power to said mixing apparatus,
a support housing outside the bag for supporting the bag during use and a raceway formed in the inner surface of the support housing for the power cable and wherein the probe housing extends into the interior of the bag such that the one or more probes are fully contained within the interior of the bag and the probe housing extends into the bag interior at a downward angle by a taper to the housing such that the inner surface of the probe housing at its lowermost point extends further into the bag interior than the top point of the probe housing.

\* \* \* \* \*